(12) United States Patent
Butler (10) Patent No.: US 10,258,386 B2
(45) Date of Patent: Apr. 16, 2019

(54) SPINAL CONSTRUCT AND METHOD

(71) Applicant: Warsaw Orthopedic, Inc, Warsaw, IN (US)

(72) Inventor: Brian A. Butler, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 9 days.

(21) Appl. No.: 15/624,481

(22) Filed: Jun. 15, 2017

(65) Prior Publication Data

US 2018/0360500 A1 Dec. 20, 2018

(51) Int. Cl.
*A61B 17/70* (2006.01)
*A61B 17/00* (2006.01)

(52) U.S. Cl.
CPC ...... *A61B 17/7043* (2013.01); *A61B 17/7002* (2013.01); *A61B 2017/00526* (2013.01)

(58) Field of Classification Search
CPC .................................. A61B 17/7032–17/7055
See application file for complete search history.

(56) References Cited

U.S. PATENT DOCUMENTS

| 5,002,542 | A | | 3/1991 | Frigg | |
|---|---|---|---|---|---|
| 5,053,034 | A | | 10/1991 | Olerud | |
| 5,474,551 | A | * | 12/1995 | Finn | A61B 17/7035 606/264 |
| 5,645,544 | A | | 7/1997 | Tai et al. | |
| 5,928,233 | A | * | 7/1999 | Apfelbaum | A61B 17/7055 606/261 |
| 5,976,135 | A | * | 11/1999 | Sherman | A61B 17/7044 606/278 |
| 6,183,473 | B1 | | 2/2001 | Ashman | |
| 6,187,005 | B1 | * | 2/2001 | Brace | A61B 17/7035 606/264 |
| 6,210,413 | B1 | * | 4/2001 | Justis | A61B 17/7041 606/254 |
| 6,231,575 | B1 | | 5/2001 | Krag | |
| 6,520,962 | B1 | | 2/2003 | Taylor et al. | |
| 6,551,318 | B1 | * | 4/2003 | Stahurski | A61B 17/7038 606/252 |
| 6,602,253 | B2 | | 8/2003 | Richelsoph et al. | |
| 6,875,211 | B2 | | 4/2005 | Nichols et al. | |
| 6,945,972 | B2 | * | 9/2005 | Frigg | A61B 17/7041 606/256 |
| 7,618,443 | B2 | * | 11/2009 | Abdou | A61B 17/6433 606/267 |
| 7,621,941 | B2 | | 11/2009 | Schlapfer et al. | |
| 7,621,942 | B2 | * | 11/2009 | Piehl | A61B 17/8061 606/279 |
| 7,674,293 | B2 | | 3/2010 | Kuiper et al. | |
| 7,799,059 | B2 | | 9/2010 | Kramer et al. | |
| 7,806,912 | B2 | | 10/2010 | Lawton et al. | |

(Continued)

*Primary Examiner* — Eduardo C Robert
*Assistant Examiner* — Michelle C Eckman (57) ABSTRACT

A spinal construct comprises a member that defines an axial cavity and includes a transverse rod. The member further defines a groove configured for disposal of a band. A part is disposed with the axial cavity and engageable with the band to provisionally fix the part relative to the member. An implant receiver is disposable with the axial cavity to move the part and engage the band to connect the member with the implant receiver. Implants, systems, instruments and methods are disclosed.

20 Claims, 8 Drawing Sheets

(56) References Cited

U.S. PATENT DOCUMENTS

| | | | |
|---|---|---|---|
| 7,833,252 B2* | 11/2010 | Justis | A61B 17/7037 606/269 |
| 7,914,531 B1* | 3/2011 | Geller | A61B 17/68 606/278 |
| 7,927,353 B2* | 4/2011 | Taylor | A61B 17/7035 606/246 |
| 8,021,399 B2 | 9/2011 | Ritland | |
| 8,147,527 B2* | 4/2012 | Hoffman | A61B 17/7055 606/280 |
| 8,167,908 B2 | 5/2012 | Ely et al. | |
| 8,246,657 B1 | 8/2012 | Samuel | |
| 8,246,662 B2* | 8/2012 | Lemoine | A61B 17/7055 606/250 |
| 8,317,834 B2* | 11/2012 | Rezach | A61B 17/7038 606/259 |
| 8,337,532 B1* | 12/2012 | McLean | A61B 17/7011 606/250 |
| 8,414,623 B2* | 4/2013 | Baker | A61B 17/705 606/264 |
| 8,556,938 B2* | 10/2013 | Jackson | A61B 17/7008 606/269 |
| 8,758,411 B1 | 6/2014 | Rayon et al. | |
| 8,834,540 B2* | 9/2014 | Purcell | A61B 17/7037 606/264 |
| 8,882,803 B2 | 11/2014 | Iott et al. | |
| 8,998,956 B2 | 4/2015 | George et al. | |
| 8,998,957 B2 | 4/2015 | Kalfas et al. | |
| 9,101,405 B2 | 8/2015 | Dickinson et al. | |
| 9,451,994 B1 | 9/2016 | Whipple et al. | |
| 9,452,006 B2* | 9/2016 | Biedermann | A61B 17/844 |
| 9,510,862 B2 | 12/2016 | Montello et al. | |
| 9,724,131 B2* | 8/2017 | Bootwala | A61B 17/7049 |
| 9,737,340 B1* | 8/2017 | Seago | A61B 17/7041 |
| 9,763,700 B1* | 9/2017 | Gregory | A61B 17/7037 |
| 9,855,078 B2* | 1/2018 | Faulhaber | A61B 17/705 |
| 9,924,975 B2* | 3/2018 | Jackson | A61B 17/7037 |
| 2003/0028191 A1* | 2/2003 | Shluzas | A61B 17/7035 606/278 |
| 2004/0210216 A1* | 10/2004 | Farris | A61B 17/7038 606/264 |
| 2005/0080420 A1* | 4/2005 | Farris | A61B 17/7037 606/261 |
| 2005/0113830 A1* | 5/2005 | Rezach | A61B 17/7037 606/60 |
| 2005/0240181 A1* | 10/2005 | Boomer | A61B 17/7041 606/914 |
| 2005/0283153 A1* | 12/2005 | Poyner | A61B 17/7044 606/53 |
| 2006/0004359 A1* | 1/2006 | Kramer | A61B 17/7035 606/301 |
| 2006/0247628 A1* | 11/2006 | Rawlins | A61B 17/7041 606/278 |
| 2007/0135817 A1* | 6/2007 | Ensign | A61B 17/7007 606/96 |
| 2007/0161987 A1* | 7/2007 | Capote | A61B 17/7037 606/86 A |
| 2007/0162008 A1* | 7/2007 | Cline, Jr. | A61B 17/7037 606/60 |
| 2007/0191840 A1* | 8/2007 | Pond, Jr. | A61B 17/7037 623/17.16 |
| 2007/0238335 A1* | 10/2007 | Veldman | A61B 17/7038 439/157 |
| 2008/0015576 A1* | 1/2008 | Whipple | A61B 17/7037 606/60 |
| 2008/0015579 A1* | 1/2008 | Whipple | A61B 17/7037 606/250 |
| 2008/0021454 A1* | 1/2008 | Chao | A61B 17/7044 606/250 |
| 2008/0021455 A1* | 1/2008 | Chao | A61B 17/7034 606/250 |
| 2008/0021456 A1* | 1/2008 | Gupta | A61B 17/7049 606/250 |
| 2008/0051783 A1* | 2/2008 | Null | A61B 17/7055 606/261 |
| 2008/0108992 A1* | 5/2008 | Barry | A61B 17/7037 606/258 |
| 2008/0161859 A1* | 7/2008 | Nilsson | A61B 17/7032 606/266 |
| 2008/0177260 A1* | 7/2008 | McKinley | A61B 17/7037 606/60 |
| 2008/0312692 A1* | 12/2008 | Brennan | A61B 17/7005 606/246 |
| 2008/0312697 A1* | 12/2008 | Butters | A61B 17/7037 606/272 |
| 2009/0036929 A1 | 2/2009 | REglos et al. | |
| 2009/0036934 A1* | 2/2009 | Biedermann | A61B 17/7037 606/301 |
| 2009/0069852 A1* | 3/2009 | Farris | A61B 17/7037 606/301 |
| 2009/0149887 A1* | 6/2009 | Schlaepfer | A61B 17/7034 606/278 |
| 2009/0216276 A1* | 8/2009 | Pasquet | A61B 17/7043 606/249 |
| 2010/0049253 A1* | 2/2010 | Miller | A61B 17/7037 606/264 |
| 2010/0094345 A1* | 4/2010 | Saidha | A61B 17/7052 606/250 |
| 2010/0125299 A1* | 5/2010 | Paul | A61B 17/7044 606/280 |
| 2010/0160974 A1* | 6/2010 | Viker | A61B 17/7037 606/301 |
| 2010/0160976 A1* | 6/2010 | Biedermann | A61B 17/7035 606/302 |
| 2010/0168800 A1* | 7/2010 | Biedermann | A61B 17/7037 606/302 |
| 2010/0168801 A1* | 7/2010 | Biedermann | A61B 17/7032 606/302 |
| 2010/0174322 A1* | 7/2010 | Abdelgany | A61B 17/7037 606/301 |
| 2010/0204735 A1* | 8/2010 | Gephart | A61B 17/7037 606/264 |
| 2011/0009911 A1* | 1/2011 | Hammill, Sr. | A61B 17/7037 606/308 |
| 2011/0087287 A1 | 4/2011 | Reeder, Jr. et al. | |
| 2011/0098753 A1* | 4/2011 | Giger | A61B 17/7035 606/305 |
| 2011/0106168 A1* | 5/2011 | Bucci | A61B 17/7032 606/264 |
| 2011/0196425 A1* | 8/2011 | Rezach | A61B 17/7035 606/278 |
| 2012/0029566 A1* | 2/2012 | Rezach | A61B 17/7038 606/264 |
| 2012/0029571 A1* | 2/2012 | Schwab | A61B 17/705 606/278 |
| 2012/0046701 A1* | 2/2012 | Gennari | A61B 17/7037 606/308 |
| 2012/0109218 A1* | 5/2012 | Farris | A61B 17/7037 606/305 |
| 2012/0172932 A1* | 7/2012 | Biedermann | A61B 17/7037 606/279 |
| 2012/0179205 A1* | 7/2012 | Miller | A61B 17/7041 606/264 |
| 2012/0179209 A1* | 7/2012 | Biedermann | A61B 17/7037 606/305 |
| 2012/0179211 A1* | 7/2012 | Biedermann | A61B 17/7037 606/328 |
| 2012/0197314 A1* | 8/2012 | Farris | A61B 17/7037 606/305 |
| 2013/0046345 A1* | 2/2013 | Jones | A61B 17/7037 606/266 |
| 2013/0053854 A1* | 2/2013 | Schoenefeld | A61B 17/1757 606/87 |
| 2013/0085536 A1* | 4/2013 | Biedermann | A61B 17/7035 606/308 |
| 2013/0096617 A1* | 4/2013 | Ballard | A61B 17/7049 606/278 |
| 2013/0110180 A1* | 5/2013 | Doubler | A61B 17/7037 606/308 |

(56) References Cited

U.S. PATENT DOCUMENTS

| | | | |
|---|---|---|---|
| 2013/0150852 A1* | 6/2013 | Shluzas | A61B 17/7032 606/65 |
| 2013/0184760 A1* | 7/2013 | Ballard | A61B 17/7041 606/278 |
| 2013/0211456 A1* | 8/2013 | Dickinson | A61B 17/7041 606/264 |
| 2013/0211457 A1* | 8/2013 | Dickinson | A61B 17/7041 606/264 |
| 2013/0218213 A1* | 8/2013 | Lemoine | A61B 17/7032 606/305 |
| 2013/0245690 A1* | 9/2013 | Bridwell | A61B 17/7038 606/278 |
| 2013/0253588 A1* | 9/2013 | Traynelis | A61B 17/7005 606/269 |
| 2013/0345754 A1* | 12/2013 | Doubler | A61B 17/7037 606/266 |
| 2014/0052189 A1* | 2/2014 | Hammer | A61B 17/7032 606/278 |
| 2014/0128918 A1* | 5/2014 | Harper | A61B 17/705 606/252 |
| 2014/0228891 A1* | 8/2014 | Hammer | A61B 17/7055 606/278 |
| 2014/0257399 A1* | 9/2014 | Rezach | A61B 17/7037 606/272 |
| 2014/0257411 A1* | 9/2014 | Rezach | A61B 17/7037 606/305 |
| 2014/0277163 A1* | 9/2014 | Kretzer | A61B 17/7049 606/278 |
| 2014/0316468 A1* | 10/2014 | Keiser | A61B 17/7052 606/252 |
| 2014/0321945 A1* | 10/2014 | Black | F16B 29/00 411/383 |
| 2015/0173816 A1* | 6/2015 | Biedermann | A61B 17/8605 606/308 |
| 2015/0201972 A1* | 7/2015 | Doubler | A61B 17/7002 606/266 |
| 2015/0282844 A1* | 10/2015 | Vedula | A61B 17/7032 606/305 |
| 2015/0282845 A1* | 10/2015 | Mirda | A61B 17/7055 606/272 |
| 2015/0313645 A1* | 11/2015 | Hansell | A61B 17/7035 606/272 |
| 2015/0320465 A1* | 11/2015 | Butler | A61B 17/8605 606/308 |
| 2016/0015429 A1* | 1/2016 | Butler | A61B 17/7035 606/278 |
| 2016/0089187 A1* | 3/2016 | Bootwala | A61B 17/7049 606/278 |
| 2016/0106473 A1* | 4/2016 | Rezach | A61B 17/7035 606/265 |
| 2016/0113684 A1* | 4/2016 | Rezach | A61B 17/7032 606/278 |
| 2016/0143665 A1* | 5/2016 | Biedermann | A61B 17/7002 606/267 |
| 2016/0220277 A1* | 8/2016 | Rezach | A61B 17/7037 |
| 2016/0262798 A1* | 9/2016 | Rezach | A61B 17/7007 |
| 2016/0262817 A1* | 9/2016 | Rezach | A61B 17/8605 |
| 2016/0287294 A1* | 10/2016 | Kubo | A61B 17/7041 |
| 2016/0317206 A1* | 11/2016 | Rezach | A61B 17/7037 |
| 2016/0367292 A1* | 12/2016 | Nichols | A61B 17/7041 |
| 2017/0027615 A1* | 2/2017 | Rezach | A61B 17/7032 |
| 2017/0079689 A1* | 3/2017 | Prevost | A61B 17/7035 |
| 2017/0079690 A1* | 3/2017 | Oberlander | A61B 17/7037 |
| 2017/0095271 A1* | 4/2017 | Faulhaber | A61B 17/7032 |
| 2017/0112540 A1 | 4/2017 | Montello et al. | |
| 2017/0245898 A1* | 8/2017 | May | A61B 17/7037 |
| 2017/0273724 A1* | 9/2017 | McLean | A61B 17/705 |
| 2017/0281247 A1* | 10/2017 | Murray | A61B 17/705 |
| 2017/0333085 A1* | 11/2017 | Jackson | A61B 17/7037 |
| 2017/0333086 A1* | 11/2017 | Jackson | A61B 17/8615 |
| 2018/0049777 A1* | 2/2018 | Rezach | A61B 17/7037 |
| 2018/0078284 A1* | 3/2018 | Faulhaber | A61B 17/7058 |
| 2018/0092668 A1* | 4/2018 | Keiser | A61B 17/7052 |
| 2018/0110548 A1* | 4/2018 | May | A61B 17/7049 |

* cited by examiner

SPINAL CONSTRUCT AND METHOD

TECHNICAL FIELD

The present disclosure generally relates to medical devices for the treatment of spinal disorders, and more particularly to a spinal implant system including a spinal construct and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, microdiscectomy, corpectomy, decompression, laminectomy, laminotomy, foraminotomy, facetectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a spinal construct is provided. The spinal construct includes a member that defines an axial cavity and includes a transverse rod. The member further defines a groove configured for disposal of a band. A part is disposed with the axial cavity and engageable with the band to provisionally fix the part relative to the member. An implant receiver is disposable with the axial cavity to move the part and engage the band to connect the member with the implant receiver. In some embodiments, implants, systems, instruments and methods are disclosed.

In one embodiment, a method of assembly for a spinal construct is provided. The method includes the steps of: engaging a part with a band disposed within a groove of a connector including a transverse rod to provisionally fix the part relative to the connector; and manually engaging an implant receiver with the part to move the part and engage the band to connect the implant receiver with the connector to comprise a spinal construct in a non-instrumented assembly.

In one embodiment, the spinal construct includes a connector defining an axial cavity. The connector includes a transverse rod and further defines an inner groove configured for disposal of a band that is expandable within the groove between a capture orientation and an expanded orientation. A sleeve is disposed with the axial cavity and includes an outer groove for disposal of the band. The sleeve engages the band to provisionally fix the sleeve in position with the connector. An implant receiver is disposable with the axial cavity to axially translate the sleeve and engage the band to connect the connector with the implant receiver.

BRIEF DESCRIPTION OF THE DRAWINGS

The present disclosure will become more readily apparent from the specific description accompanied by the following drawings, in which.

DETAILED DESCRIPTION

The exemplary embodiments of a surgical system and related methods of use disclosed are discussed in terms of medical devices for the treatment of musculoskeletal disorders and more particularly, in terms of a surgical system and method for treatment of a spine disorder. In some embodiments, the present system includes a spinal construct having a transverse rod, an implant receiver and a spinal rod. In some embodiments, the systems and methods of the present disclosure are employed with a spinal joint fusion, for example, with a cervical, thoracic, lumbar and/or sacral region of a spine.

In some embodiments, the present system includes a spinal construct, such as, for example, a modular lateral connector. In some embodiments, the connector is configured for a modular connection with an implant receiver. In some embodiments, the present system provides a modular connector that allows selection of alternately configured implant receivers, such as, for example, a top loading receiver, a side loading receiver and/or a closed receiver. In some embodiments, the various implant receivers are provided in a kit. In some embodiments, the modular connector facilitates reducing an overall size of the kit as variously sized connectors can be connected with various receiver configurations and/or sizes. In some embodiments, the present system facilitates connection of the connector and the receiver when an anatomy is disposed in an orientation that disrupts alignment of construct components.

In some embodiments, the present system is employed with a method of assembly including the step of inserting a head of an implant receiver into a post of a modular connector. In some embodiments, the method includes the step of engaging the head to force a centering sleeve in a downward direction relative to the connector. In some embodiments, the method includes the step of fully engaging the head of the implant receiver such that a snap ring permanently assembles the implant receiver with the connector. In some embodiments, the method includes the step of engaging a setscrew with the implant receiver to fix a spinal rod with the implant receiver and the connector such that the setscrew and a top surface of the post of the connector engage the spinal rod.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a spinal construct, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-4, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Figure 8:
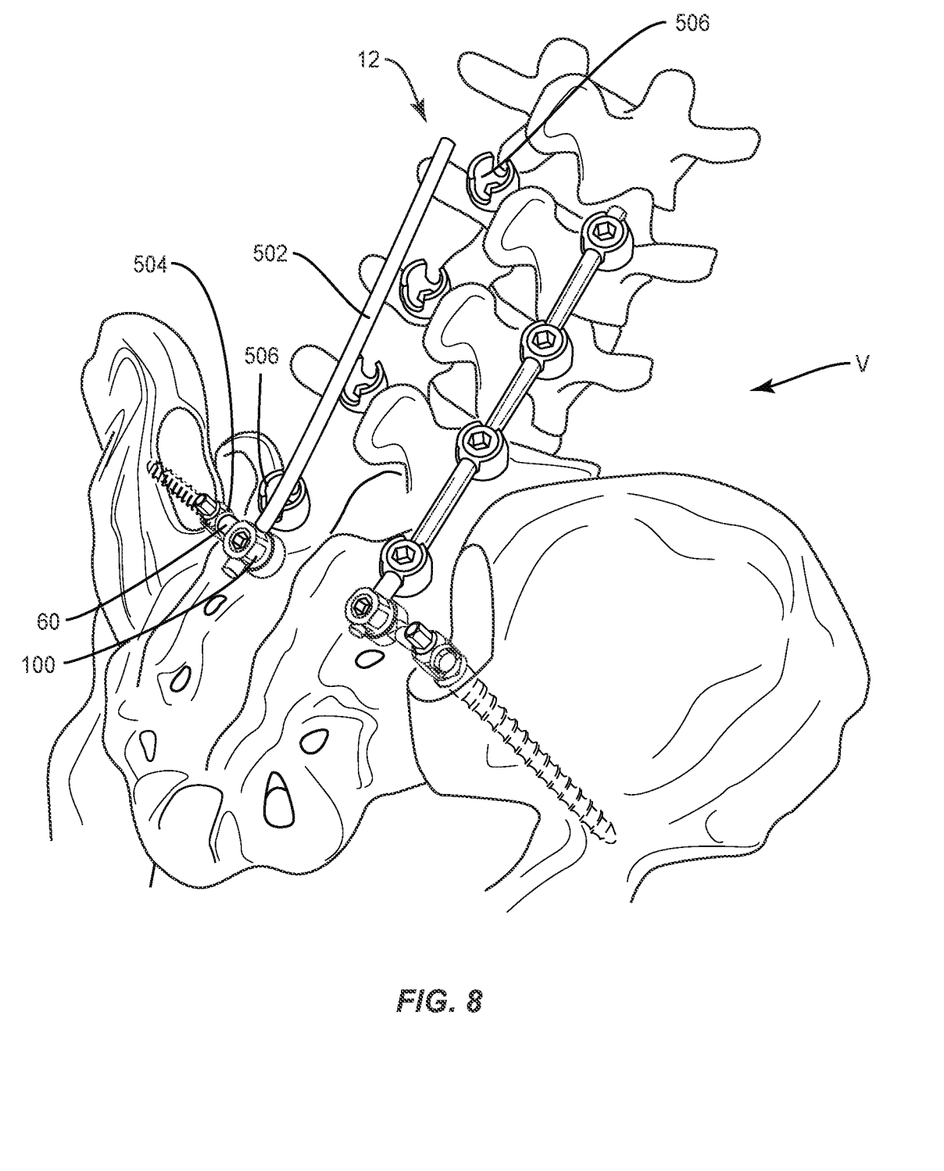
FIG. 8 is a perspective view of components of one embodiment of a spinal implant system in accordance with the principles of the present disclosure disposed with vertebrae.

Spinal implant system 10 includes a spinal construct 12. Spinal implant system 10 is employed, for example, with an open or mini-open, minimal access and/or minimally invasive including percutaneous surgical technique and may include one or more spinal constructs 12 for treatment at a surgical site within a body of a patient, for example, a section of a spine to treat various spine pathologies, such as those described herein. In some embodiments, the components of spinal implant system 10 are configured to deliver and introduce components of a spinal construct 12 that includes implants, such as, for example, one or more receivers, spinal rods, bodies, sleeves, connectors, plates and/or fasteners. Spinal construct 12 forms one or more components of a surgical treatment implanted with tissue for positioning and alignment to stabilize a treated section of vertebrae V (for example, as shown in FIG. 8).

Spinal construct 12 includes a connector 14. Connector 14 includes a member, such as, for example, a body 16 engageable with an implant receiver 100, as described herein. Body 16 defines an axis X1. Body 16 includes a wall 18 having a surface 20 that defines a cavity 22. Wall 18 extends between a surface 24 and a surface 26. In some embodiments, surfaces 24, 26 include a planar configuration and extend perpendicular to axis X1. Cavity 22 is configured for disposal of receiver 100, as described herein.

Cavity 22 includes a substantially circular cross section. In some embodiments, cavity 22 may have various cross section configurations, such as, for example, oval, oblong, triangular, rectangular, square, polygonal, irregular, uniform, non-uniform, variable and/or tapered. In some embodiments, surface 20 may include gripping elements or surface 20 may be, for example, rough, arcuate, undulating, mesh, porous, semi-porous, dimpled and/or textured to facilitate engagement with implant receiver 100.

Body 16 includes a surface 30. Surface 30 defines a cavity, such as, for example, a circumferential channel 32 configured for disposal of a band, such as, for example, a circumferential ring 34. In some embodiments, ring 34 includes a selected height and a selected width. Ring 34 includes a circumference that extends between ends of ring 34. In some embodiments, the ends define a gap. In some embodiments, the gap is sized such that the gap has a thickness that is less than the height and the width. In some embodiments, upon disposal of ring 34 with groove 32, the surface of groove 32 resists and/or prevents axial translation of ring 34 relative to axis X1.

Surface 30 defines a slot 40 configured for disposal of a part, such as, for example, a sleeve 42. Sleeve 42 includes a surface 44 that defines a cavity, such as, for example, a groove 46. In some embodiments, groove 46 extends about all or a portion of surface 44. Groove 46 includes a surface 48 and a surface 50. Surface 48 is disposed at an angle relative to axis X1 to define a ramp. Surface 50 is disposed at an angle relative to axis X1 to define a ramp. The ramps of surfaces 48, 50 are oriented in spaced apart relation. An intermediate surface 52 is disposed between the ramps. Surface 52 is substantially even and circumferentially disposed about sleeve 42. In some embodiments, the ramps of surfaces 48, 50 are selectively inclined to resist and/or prevent displacement of ring 34 from channel 32 to provisionally fix sleeve 42 with body 16. In some embodiments, the inclination of the ramps of surfaces 48, 50 facilitate disengagement of ring 34 from groove 36 upon axial translation of sleeve 42, as described herein. In some embodiments, surfaces 48, 50 are oriented substantially perpendicular to axis X1.

Figure 5:
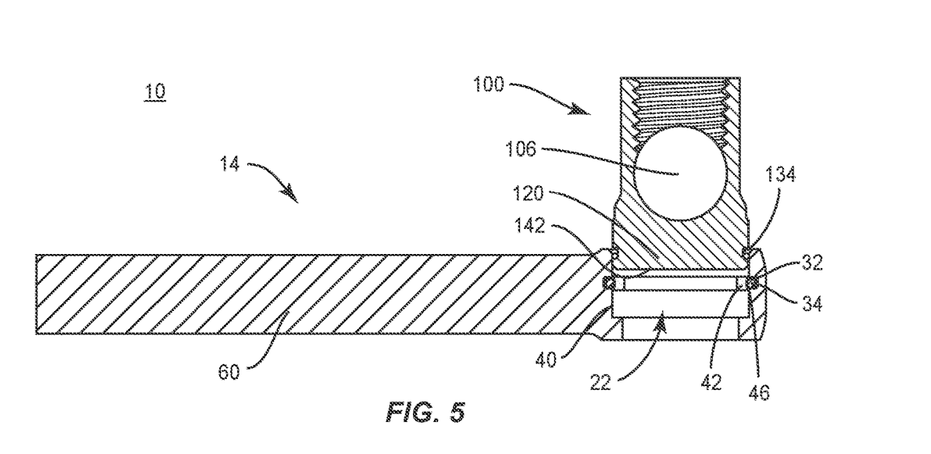
FIG. 5 is a cross section view of components of the system shown in FIG. 1.
Figure 7:
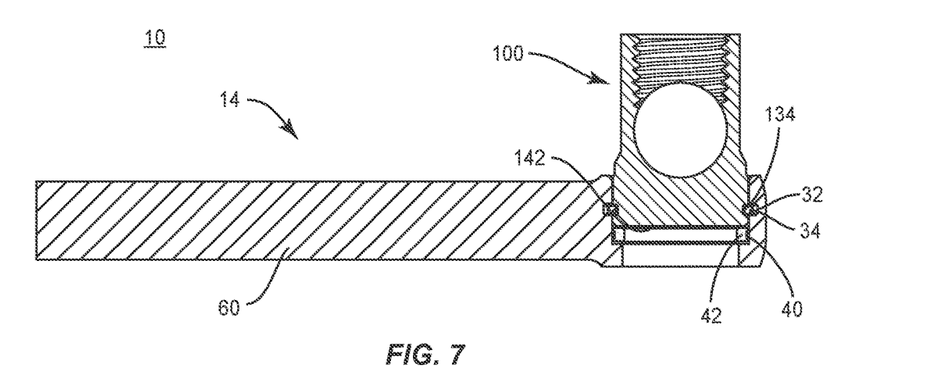
FIG. 7 is a cross section view of the components of the system shown in FIG. 1.

Sleeve 42 is configured for translation within slot 40 along surface 30. Sleeve 42 translates with implant receiver 100 within slot 40. Translation of sleeve 42 within slot 40 moves sleeve 42 between a configuration, as shown in FIG. 5, such that ring 34 is disposed within channel 32 and groove 46 to provisionally fix sleeve 42 relative to body 16 and a configuration, as shown in FIG. 7, such that ring 34 remains disposed within channel 32 and disposed with groove 134 to fix implant receiver 100 with body 16, as described herein.

Figure 1:
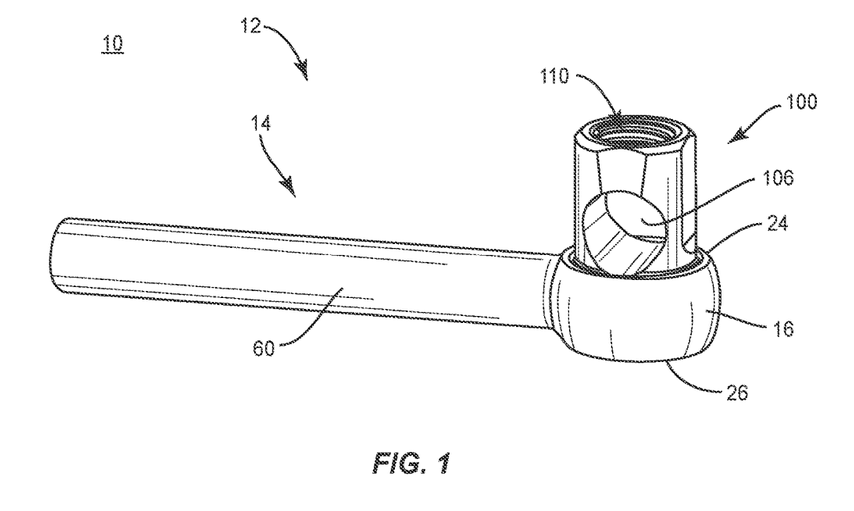
FIG. 1 is a perspective view of components of one embodiment of a spinal implant system in accordance with the principles of the present disclosure.
Figure 2:
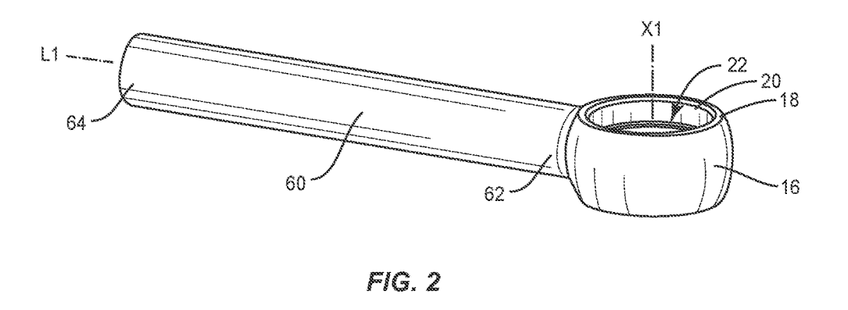
FIG. 2 is a perspective view of components of the system shown in FIG. 1.
Figure 3:
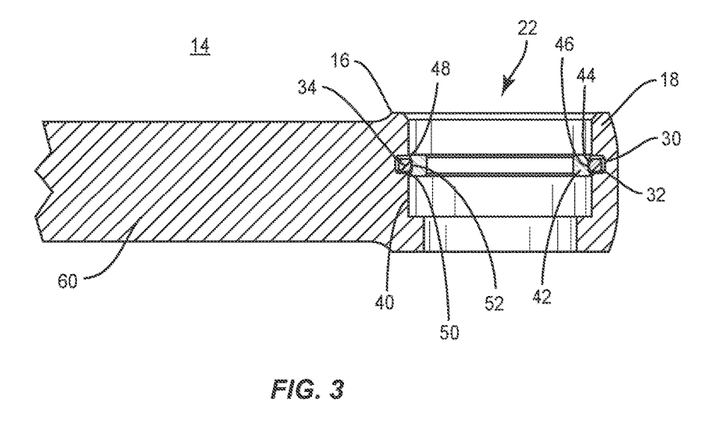
FIG. 3 is a cross section view of the components shown in FIG. 2.

A rod 60 extends from wall 18. Rod 60 defines an axis L1, as shown in FIG. 2. Rod 60 extends between an end 62 and an end 64. In some embodiments, rod 60 may have various cross section configurations, such as, for example, circular, oval, oblong, polygonal, irregular, uniform, non-uniform, variable, offset and/or tapered. In some embodiments, end 64 is configured for connection with a receiver of one or a plurality of bone screws, as described herein. In some embodiments, end 64 is connectable with tissue via a fastener, as described herein, and/or with one or more components of spinal construct 12 via a fastener, as described herein.

In some embodiments, axis L1 is disposed perpendicular to axis X1. In some embodiments, all or a portion of rod 60 extends in the same plane as body 16. In some embodiments, all or a portion of rod 60 extends offset relative to body 16. In some embodiments, axis L1 may be disposed at alternate orientations relative to axis X1, such as, for example, transverse and/or other angular orientations such as acute or obtuse, coaxial and/or may be offset or staggered. In some embodiments, rod 60 is monolithically formed with body 16. In some embodiments, rod 60 may be integrally connected or include fastening elements and/or instruments for connection with body 16.

In some embodiments, rod 60 is oriented to extend transverse to an existing spinal rod implant. In some embodiments, rod 60 is oriented to extend parallel to an existing spinal rod implant. In some embodiments, connector 14 is configured to revise an existing spinal construct by extending an existing spinal rod one or more spinal levels without removal of the existing spinal rod such that connector 14 allows for extension of rod 60 while providing clearance to accommodate the existing spinal rod.

Figure 4:
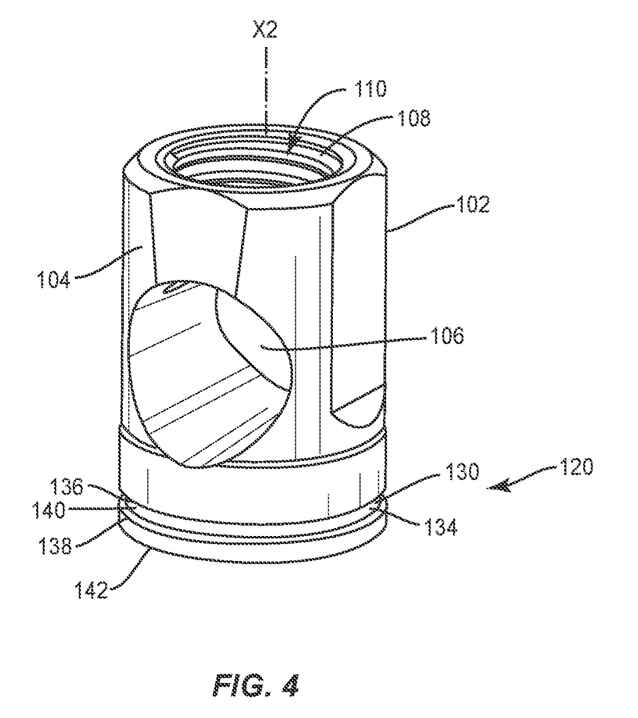
FIG. 4 is a perspective of components of the system shown in FIG. 1.

Implant receiver 100 extends along and defines an axis X2. Implant receiver 100 includes a pair of spaced apart arms 102, 104, as shown in FIG. 4. Arms 102, 104 are connected at ends thereof such that implant receiver 100 defines a closed implant cavity, such as, for example, a spinal rod slot 106. Rod slot 106 is substantially circular. In some embodiments, arms 102, 104 each include an arcuate outer surface extending between a pair of side surfaces. In some embodiments, at least one of the outer surfaces and the side surfaces of arms 102, 104 have at least one recess or cavity therein configured to receive an insertion tool. In some embodiments, all or only a portion of rod slot 106 may have alternate cross section configurations, such as, for example, U-shaped, V-shaped, W-shaped, oval, oblong triangular, square, polygonal, irregular, uniform, non-uniform, offset, staggered, and/or tapered.

Implant receiver 100 includes an inner surface 108 that defines a cavity 110 configured for disposal of coupling member, such as, for example, a setscrew (not shown). Cavity 110 is disposed in communication with rod slot 106 to retain a spinal rod within cavity 106. Surface 108 includes a thread form configured for engagement with the setscrew. The setscrew is configured to capture a spinal rod disposed with rod slot 106. Upon tightening of setscrew, the spinal rod is captured between the setscrew and surface 24 and/or the surface defining slot 106. In some embodiments, implant receiver 100 may be disposed with the coupling member in alternate fixation configurations, such as, for example, friction fit, pressure fit, locking protrusion/recess, locking keyway and/or adhesive. In some embodiments, all or only a portion of surface 24, surface 108 and/or the surface defining slot 106 may have alternate surface configurations to enhance engagement with the spinal rod and/or setscrew, such as, for example, rough, arcuate, undulating, mesh, porous, semi-porous, dimpled and/or textured. In some embodiments, implant receiver 100 may include alternate configurations, such as, for example, closed, open and/or side access, similar to that described herein.

Implant receiver 100 includes a base 120. Base 120 includes a surface 130 that defines a cavity, such as, for example, a groove 134. Groove 134 includes a surface 136 and a surface 138. Surfaces 136, 138 are oriented substantially perpendicular to axis X2. In some embodiments, surfaces 136, 138 may be disposed in various orientations and/or inclinations, such as, for example, transverse and/or at angular orientations, such as acute or obtuse relative to axis X2. Surface 136 is oriented in spaced apart relation relative to surface 138. An intermediate surface 140 is disposed between surfaces 136, 138. Surface 140 is substantially even and circumferentially disposed about groove 134. In some embodiments, surfaces 136, 138, 140 may be disposed about all or only a portion of groove 134. Groove 134 is configured for disposal of ring 34 to prevent displacement of ring 34 from channel 32 and to permanently fix implant receiver 100 with body 16, as shown in FIG. 7. Base 120 includes a surface 142. Surface 142 is configured to engage sleeve 42 during axial translation of implant receiver 100 relative to body 16 within slot 42, as described herein.

Figure 6:
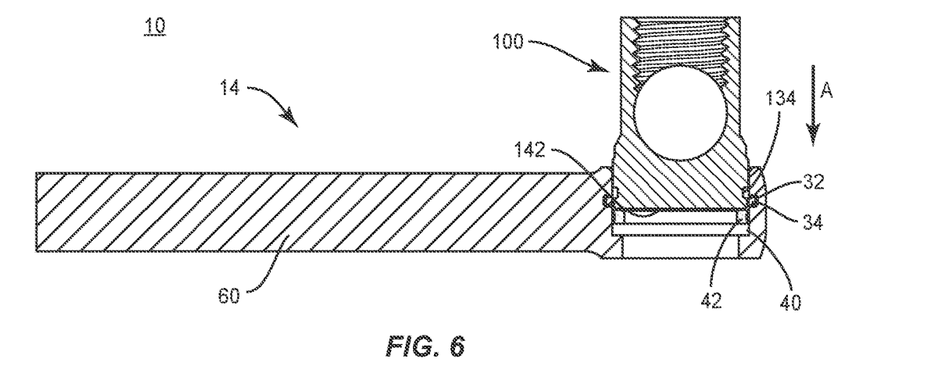
FIG. 6 is a cross section view of the components of the system shown in FIG. 1.

For example, implant receiver 100 is disposed in alignment with cavity 22, as shown in FIG. 5. Surface 142 of implant receiver 100 engages sleeve 42 to release sleeve 42 from ring 34. As implant receiver 100 engages sleeve 42 and translates, in a direction shown by arrow A in FIG. 6, the ramp of surface 48 engages ring 34 and surface 48 slides over ring 34 to release sleeve 42 from ring 34. Ring 34 is expanded into channel 32. With ring 34 expanded into channel 32, implant receiver 100 axially translates relative to body 16 within slot 40 to align groove 134 with channel 32. Expansion of ring 34 via engagement with surface 48 facilitates axial translation of receiver 14 into slot 40. Alignment of groove 134 with channel 32 allows ring 34 to resiliently contract to the capture orientation, as shown in FIG. 7, for disposal of ring 34 within groove 134 and channel 32. Ring 34 is fixed within channel 32 and groove 134. Surfaces 136, 138 resist and/or prevent disengagement of ring 34 from channel 32 and groove 134 to permanently assemble implant receiver 100 with body 16.

In some embodiments, implant receiver 100 is manually engageable with body 16 in a non-instrumented assembly such that ring 34 translates from disposal with channel 32 and groove 46 to disposal with channel 32 and groove 134, as described herein. In some embodiments, manual engagement and/or non-instrumented assembly of implant receiver 100 and body 16 includes coupling without use of separate and/or independent instrumentation engaged with implant receiver 100 components to effect assembly. In some embodiments, manual engagement and/or non-instrumented assembly includes a practitioner, surgeon and/or medical staff grasping implant receiver 100 and body 16 and forcibly assembling the components. In some embodiments, manual engagement and/or non-instrumented assembly includes a practitioner, surgeon and/or medical staff grasping implant receiver 100 and body 16 and forcibly snap fitting the components together, as described herein. In some embodiments, manual engagement and/or non-instrumented assembly includes a practitioner, surgeon and/or medical staff grasping implant receiver 100 and body 16 and forcibly pop fitting the components together, as described herein. In some embodiments, a force in a range of 2-50 N is required to manually engage implant receiver 100 and body 16 and forcibly assemble the components. For example, a force in a range of 2-50 N is required to snap fit and/or pop fit assemble implant receiver 100 and body 16. In some embodiments, a force in a range of 5-10 N is required to manually engage implant receiver 100 and body 16 and forcibly assemble the components. For example, a force in a range of 5-10 N is required to snap fit and/or pop fit assemble implant receiver 100 and body 16. In some embodiments, implant receiver 100 is manually engaged with body 16 in a non-instrumented assembly, as described herein, such that removal of implant receiver 100 and connector 14 requires a force and/or a pull-out strength of at least 5000 N. In some embodiments, this configuration provides manually engageable components that are assembled without instrumentation, and subsequent to assembly, the assembled components have a selected pull-out strength and/or can be pulled apart, removed and/or separated with a minimum required force. In some embodiments, spinal construct 12 includes one or a plurality of implant receivers 100 and/or bodies 16 to form connector 14.

Figure 9:
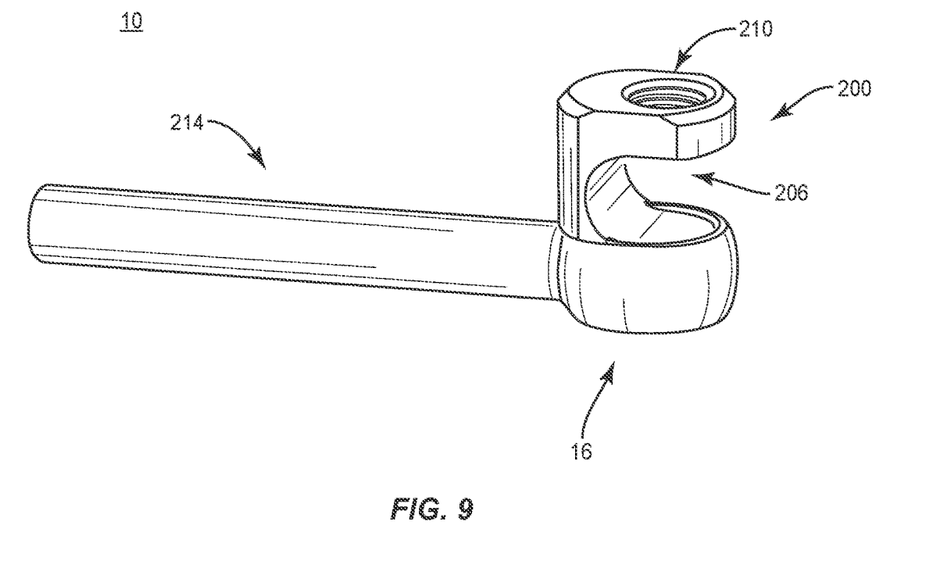
FIG. 9 is a perspective view of components of one embodiment of a spinal implant system in accordance with the principles of the present disclosure.
Figure 10:
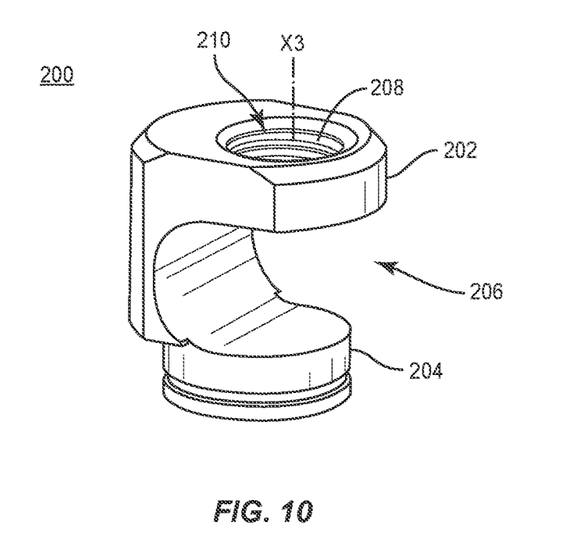
FIG. 10 is a perspective view of components of the system shown in FIG. 9.

In some embodiments, as shown in FIGS. 9 and 10, spinal implant system 10, similar to the systems and methods described herein, includes a connector 214, similar to connector 14 described herein, which includes an implant receiver 200, similar to implant receiver 100 described herein. Implant receiver 200 is engageable with body 16 for assembly therewith, similar to that described herein, and comprise components of a spinal construct disposed with vertebrae. In some embodiments, spinal implant system 10 includes a kit of one or a plurality of implant receivers, for example, receivers 100, 200, which are selectively interchangeable with body 16 to comprise a selected connector for assembly of a spinal construct disposed with vertebrae.

Implant receiver 200 includes a pair of spaced apart arms 202, 204 that define an implant cavity 206 therebetween configured for disposal of a spinal rod, similar to that described herein. Arms 202, 204 each extend transverse to an axis X3 of implant receiver 200. In some embodiments, arm 202 and/or arm 204 may be disposed at alternate orientations, relative to axis X3, such as, for example, perpendicular and/or other angular orientations such as acute or obtuse and/or may be offset or staggered. Arms 202, 204 define a lateral opening of implant cavity 206 that is configured for lateral or side-loading a spinal rod with implant receiver 200. Implant receiver 200 includes an inner surface 208 that defines a cavity 210 configured for disposal of coupling member, similar to that described with regard to receiver 100.

Figure 11:
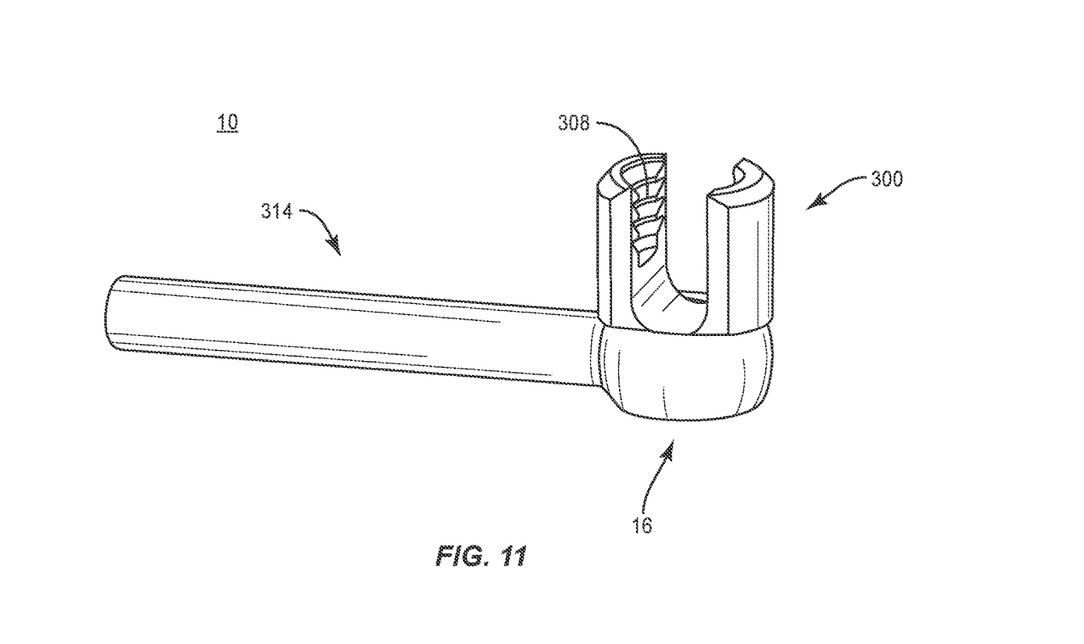
FIG. 11 is a perspective view of components of one embodiment of a spinal implant system in accordance with the principles of the present disclosure.
Figure 12:
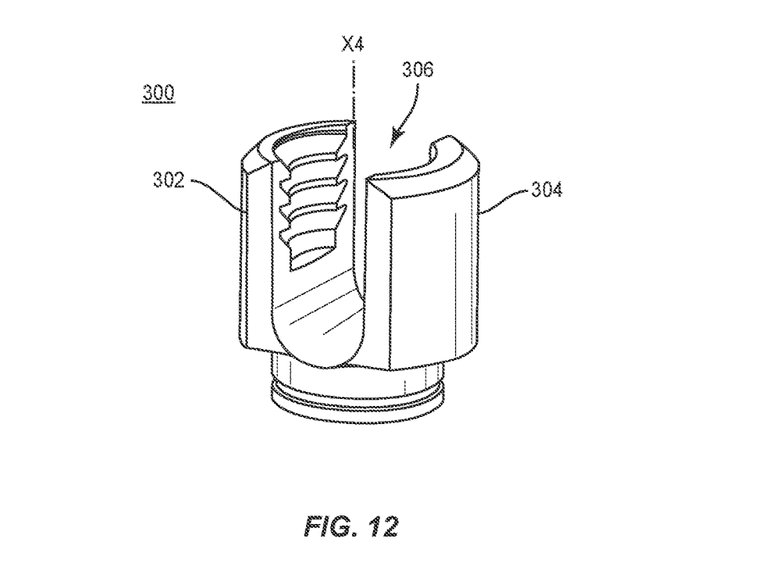
FIG. 12 is a perspective view of components of the system shown in FIG. 11.

In some embodiments, as shown in FIGS. 11 and 12, spinal implant system 10, similar to the systems and methods described herein, includes a connector 314, similar to connector 14 described herein, which includes an implant receiver 300, similar to implant receiver 100 described herein. Implant receiver 300 is engageable with body 16 for assembly therewith, similar to that described herein, and comprise components of a spinal construct disposed with vertebrae. In some embodiments, spinal implant system 10 includes a kit of one or a plurality of implant receivers, for example, receivers 100, 200, 300, which are selectively interchangeable with body 16 to comprise a selected connector for assembly of a spinal construct disposed with vertebrae.

Implant receiver 300 includes a pair of spaced apart arms 302, 304 that define an implant cavity 306 therebetween configured for disposal of the spinal rod, similar to that described herein. Arms 302, 304 each extend parallel to an axis X4 of implant receiver 300. In some embodiments, arm 302 and/or arm 304 may be disposed at alternate orientations, relative to axis X4, such as, for example, transverse and/or other angular orientations such as acute or obtuse and/or may be offset or staggered. Arms 302, 304 define an upper or top opening of implant cavity 306 that is configured for top loading a spinal rod with implant receiver 300. Implant receiver 300 includes an inner surface 308 that defines a portion of cavity 306 and is engageable with a coupling member, similar to that described with regard to receiver 100.

In assembly, operation and use, as shown in FIGS. 5-8, spinal implant system 10, similar to the systems and methods described herein, is disposed with tissue, such as, for example, vertebrae V for treatment of a spinal disorder, such as those described herein, affecting a section of a spine of a patient. In some embodiments, one or all of the components of spinal implant system 10 can be delivered as a pre-assembled device or can be assembled in situ.

An incision is made in the body of a patient and a cutting instrument (not shown) creates a surgical pathway for implantation of components of spinal implant system 10 adjacent a surgical site including vertebrae V. A preparation instrument (not shown) can be employed to prepare tissue surfaces of vertebrae V, as well as for aspiration and irrigation of a surgical region.

In some embodiments, spinal implant system 10 includes a kit including one or a plurality of implant receivers, for example, receivers 100, 200, 300, and/or alternate embodiments thereof as described herein, which are selectively interchangeable with body 16 to comprise a selected connector for assembly of a spinal construct 12 disposed with vertebrae V. Body 16, as described herein, is connectable with an interchangeable receiver having a selected size or configuration to form a selected connector, as described herein. The kit of implant receivers includes one or a plurality of implant receivers configured for use with surgical treatment, which may be selected to provide a modular connector for adaptation or adjustment to connect with one or more components of spinal construct 12 and/or tissue. The implant receiver can be selected according to the configuration and/or dimension of the components of spinal construct 12 and/or tissue, for example, a closed receiver 100, a side-loading receiver 200 and/or a top-loading receiver 300. Body 16, the selected implant receiver and one or a plurality of spinal implants, such as, for example, spinal rods can be delivered or implanted as a pre-assembled device or can be assembled in situ. The components of spinal implant system 10 may be may be completely or partially revised, removed or replaced.

For example, an implant receiver 100 is selected from the plurality of receivers of the kit of spinal implant system 10. Body 16 is interchangeable and engageable with implant receiver 100 to form connector 14 of spinal construct 12. Body 16 includes sleeve 42 and ring 34, as described herein. In some embodiments, ring 34 is disposed with channel 32 and groove 46 in a contracted and/or capture orientation to provisionally resist and/or prevent displacement of ring 34 from channel 32, as shown in FIG. 5. Ring 34 is configured to provisionally fix sleeve 42 relative to body 16.

Implant receiver 100 is disposed in alignment with cavity 22, as shown in FIG. 5. Implant receiver 100 engages sleeve 42 to release sleeve 42 from ring 34, as described herein. Ring 34 is expanded into channel 32 and implant receiver 100 axially translates relative to body 16 within slot 40 to align groove 134 with channel 32. Alignment of groove 134 with channel 32 allows ring 34 to resiliently contract to the capture orientation, as shown in FIG. 7, for disposal of ring 34 within groove 134 and channel 32. Ring 34 is fixed within channel 32 and groove 134. Surfaces 136, 138 resist and/or prevent disengagement of ring 34 from channel 32 and groove 134 to permanently assemble implant receiver 100 with body 16.

Connector 14 is connected with components of spinal construct 12, which includes a spinal rod 502 and a bone fastener 504. Spinal rod 502 is attached with vertebrae V via bone fasteners 506. In some embodiments, bone fastener 504 and/or bone fasteners 506 can be attached with sacral tissue, iliac tissue and/or one or more vertebra. Connector 14 is moveable relative to spinal rod 502 and bone fastener 504 for orientation and connection therewith. Connector 14 is oriented and/or manipulated such that spinal rod 502 is disposed with implant cavity 106 of implant receiver 100 and rod 60 is disposed with a receiver of bone fastener 504. A setscrew engages implant receiver 100 and is disposed in a locked orientation to lock spinal rod 502 with implant receiver 100. As such, spinal rod 502 is fixed in a selected position and orientation with spinal construct 12 and/or vertebrae V. A setscrew engages the receiver of bone fastener 504 to fix rod 60 therewith in a selected position and orientation with spinal construct 12 and/or vertebrae V. In some embodiments, connector 14 is connected with an existing spinal rod and bone fastener such that connector 14 extends the existing spinal rod to form a revised spinal construct.

In some embodiments, spinal implant system 10 can include one or a plurality of bone fasteners such as those described herein and/or fixation elements, which may be employed with a single vertebral level or a plurality of vertebral levels. In some embodiments, the bone fasteners may be engaged with vertebrae in various orientations, such as, for example, series, parallel, offset, staggered and/or alternate vertebral levels. In some embodiments, the bone fasteners may be configured as multi-axial screws, sagittal angulation screws, pedicle screws, mono-axial screws, uni-planar screws, fixed screws, anchors, tissue penetrating screws, conventional screws, expanding screws. In some embodiments, the bone fasteners may be employed with wedges, anchors, buttons, clips, snaps, friction fittings, compressive fittings, expanding rivets, staples, nails, adhesives, posts, connectors, fixation plates and/or post.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

In some embodiments, the use of microsurgical and image guided technologies may be employed to access, view and repair spinal deterioration or damage, with the aid of spinal implant system 10. The components of spinal implant system 10 can be made of radiolucent materials such as polymers. Radiomarkers may be included for identification under x-ray, fluoroscopy, CT or other imaging techniques.

Figure 13:
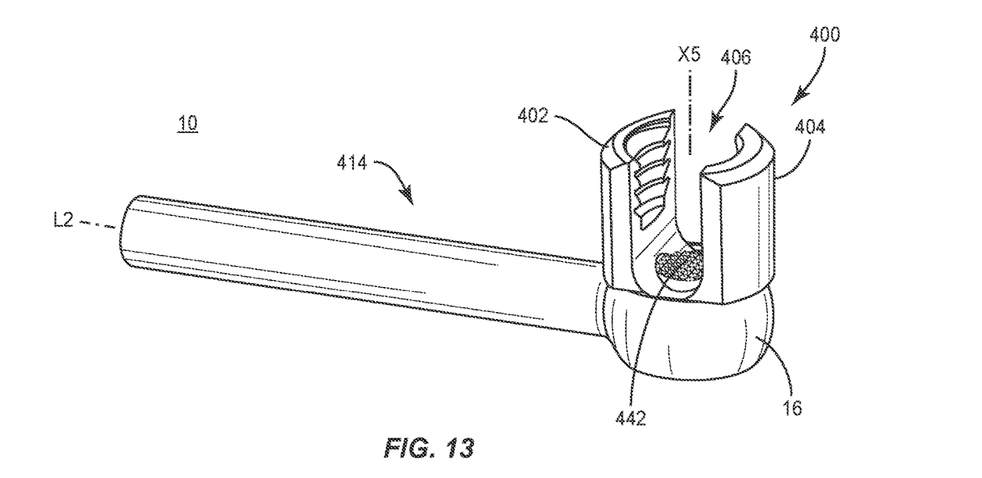
FIG. 13 is a perspective view of components of one embodiment of a spinal implant system in accordance with the principles of the present disclosure.
Figure 14:
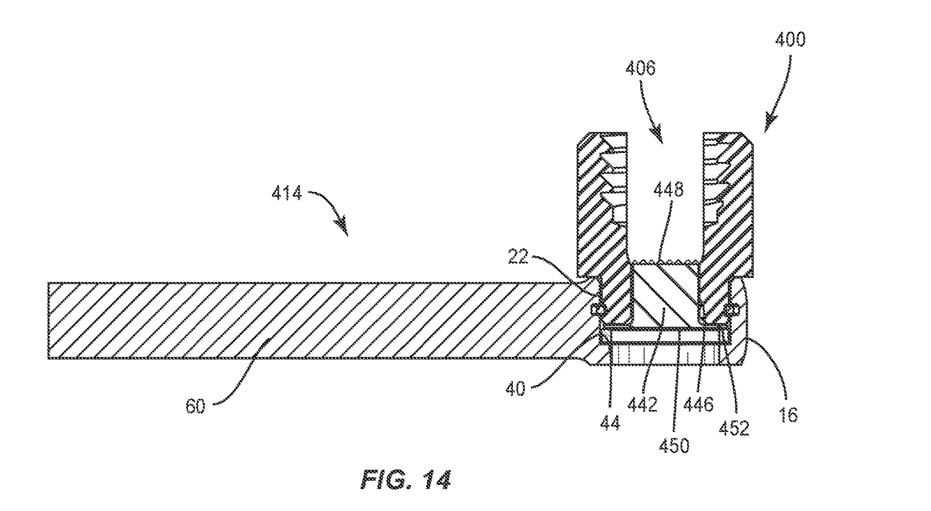
FIG. 14 is a cross section view of the components shown in FIG. 13.

In one embodiment, as shown in FIGS. 13 and 14, spinal implant system 10, similar to the systems and methods described herein, includes a connector 414, similar to connector 14 described herein, which includes an implant receiver 400, similar to implant receiver 100 described herein. Implant receiver 400 is engageable with body 16 for assembly therewith, similar to that described herein, and comprise components of a spinal construct disposed with vertebrae. In some embodiments, spinal implant system 10 includes a kit of one or a plurality of implant receivers, for example, receivers 100, 200, 300, 400, which are selectively interchangeable with body 16 to comprise a selected connector for assembly of a spinal construct disposed with vertebrae.

Implant receiver 400 includes a pair of spaced apart arms 402, 404 that define an implant cavity 406 therebetween configured for disposal of the spinal rod, similar to that described herein. Arms 402, 404 each extend parallel to an axis X5 of implant receiver 400. In some embodiments, arm 402 and/or arm 404 may be disposed at alternate orientations, relative to axis X5, such as, for example, transverse and/or other angular orientations such as acute or obtuse and/or may be offset or staggered. Arms 402, 404 define an upper or top opening of implant cavity 406 that is configured for top loading a spinal rod with implant receiver 400. Implant receiver 400 includes an inner surface 408 that defines a portion of implant cavity 406 and is engageable with a coupling member, similar to that described with regard to receiver 100.

Body 16, as described herein, defines cavity 22, which is configured for disposal of receiver 400, similar to that described herein. Body 16 defines slot 40, which is configured for disposal of a part, such as, for example, a crown 442 and sleeve 44, as described herein. Crown 442 includes a wall 446 having an end surface 448 and an end surface 450. Crown 442 extends through cavity 22 and surface 448 is disposed with implant cavity 406 for engagement with a spinal rod. Surface 448 includes a knurled configuration that facilitates engagement with a spinal rod. The knurled configuration of surface 448 extends through an opening of implant receiver 400 to engage a spinal rod. Surface 450 includes a flange 452 configured for engagement with sleeve 44. Flange 452 is disposed between implant receiver 400 and sleeve 44, as shown in FIG. 14.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
    a member defining an axial cavity and including a transverse rod, the member further defining a groove configured for disposal of a band;
    a part disposed with the axial cavity and engageable with the band to provisionally fix the part relative to the member; and
    an implant receiver being disposable with the axial cavity to move the part and engage the band to connect the member with the implant receiver, the implant receiver comprising a base defining an outer groove for disposal of the band to connect the member with the implant receiver, the outer groove extending continuously about an entire circumference of the base.

2. A spinal construct as recited in claim 1, wherein the implant receiver is manually engageable with the part to connect the member with the implant receiver in a non-instrumented assembly.

3. A spinal construct as recited in claim 1, wherein the member and the implant receiver are engageable in a snap-fit assembly.

4. A spinal construct as recited in claim 1, wherein the member and the implant receiver are engageable in a pop-on assembly.

5. A spinal construct as recited in claim 1, wherein the implant receiver is selected from a plurality of alternate implant receivers and is engageable with the part and the band such that the member is interchangeable with the plurality of implant receivers.

6. A spinal construct as recited in claim 1, wherein the part includes a sleeve that defines an outer groove for disposal of the band to provisionally fix the sleeve relative to the member.

7. A spinal construct as recited in claim 1, wherein the band is expandable within the groove between a capture orientation and an expanded orientation.

8. A spinal construct as recited in claim 1, wherein the rod is monolithically formed with the member.

9. A spinal construct as recited in claim 1, further comprising a crown disposable with the axial cavity.

10. A spinal construct as recited in claim 9, wherein the implant receiver defines an implant cavity and the crown extends through the implant receiver into the implant cavity.

11. A spinal construct as recited in claim 10, wherein crown includes a knurled surface disposed in the implant cavity.

12. A spinal construct as recited in claim 1, wherein the member includes a body comprising opposite first and second surfaces, the first and second surfaces being free of splines, the axial cavity extending through the first and second surfaces, the first and second surfaces defining a maximum thickness of the body, the transverse rod extending from the body.

13. A method of assembly for a spinal construct, the method comprising the steps of:
    engaging a part with a band disposed within a groove of a connector including a transverse rod to provisionally fix the part relative to the connector; and
    manually engaging an implant receiver with the part to move the part and engage the band to connect the implant receiver with the connector to comprise a spinal construct in a non-instrumented assembly, wherein manually engaging an implant receiver with the part comprises positioning the band within an outer groove in a base of the implant receiver, the outer groove extending continuously about an entire circumference of the base.

14. A method as recited in claim 13, wherein the implant receiver is selected from a plurality of alternate implant receivers to comprise a spinal construct having a selected configuration and the implant receiver is engageable with the part and the band such that the connector is interchangeable with the plurality of implant receivers.

15. A method as recited in claim 13, wherein the step of manually engaging includes snap fitting the implant receiver with the connector.

16. A method as recited in claim 13, wherein the connector includes a crown and the step of manually engaging includes disposing the implant receiver with the crown.

17. A method as recited in claim 13, wherein the band is expandable within the groove between a capture orientation and an expanded orientation.

18. A spinal construct comprising:
a body defining an axial cavity and including a transverse rod, the body further defining an inner groove configured for disposal of a band that is expandable within the groove between a capture orientation and an expanded orientation;
a sleeve disposed with the axial cavity and including an outer groove for disposal of the band, the sleeve engaging the band to provisionally fix the sleeve in position with the connector; and
an implant receiver being disposable with the axial cavity to axially translate the sleeve and engage the band to connect the body with the implant receiver, the implant receiver comprising a base defining an outer groove for disposal of the band to connect the body with the implant receiver, the outer groove extending continuously about an entire circumference of the base.

19. A spinal construct as recited in claim 18, wherein the body and the implant receiver are engageable in a pop-on assembly.

20. A spinal construct as recited in claim 18, wherein the implant receiver is selected from a plurality of alternate implant receivers and is engageable with the sleeve and the band such that the body is interchangeable with the plurality of implant receivers.

* * * * *

UNITED STATES PATENT AND TRADEMARK OFFICE
CERTIFICATE OF CORRECTION

PATENT NO. : 10,258,386 B2
APPLICATION NO. : 15/624481
DATED : April 16, 2019
INVENTOR(S) : Brian A. Butler Page 1 of 1

It is certified that error appears in the above-identified patent and that said Letters Patent is hereby corrected as shown below:

On the Title Page

In item (71), under "Applicant", in Column 1, Line 1, delete "Warsaw Orthopedic, Inc," and insert -- Warsaw Orthopedic, Inc., --, therefor.

In the Specification

In Column 7, Line 12, delete "cavity 106." and insert -- cavity 110. --, therefor.

In Column 7, Line 62, delete "receiver 14" and insert -- receiver 100 --, therefor.

Signed and Sealed this
Fifth Day of November, 2019

Andrei Iancu
*Director of the United States Patent and Trademark Office*